(12) United States Patent
Besson et al.

(10) Patent No.: US 6,459,754 B1
(45) Date of Patent: Oct. 1, 2002

(54) METHODS AND APPARATUS FOR CONE BEAM MULTISLICE CT CORRECTION

(75) Inventors: Guy M. Besson, Wauwatosa; Sarah K. Patch, Milwaukee, both of WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/428,183

(22) Filed: Oct. 27, 1999

(51) Int. Cl.$^7$ ................................................. A61B 6/03
(52) U.S. Cl. .............................. 378/4; 378/15; 378/901
(58) Field of Search ........................... 378/4, 8, 15, 901

(56) References Cited

U.S. PATENT DOCUMENTS

| | | | | |
|---|---|---|---|---|
| 5,377,250 A | * | 12/1994 | Hu | ............................. 378/15 |
| 5,400,255 A | | 3/1995 | Hu | |
| 5,430,783 A | | 7/1995 | Hu et al. | |
| 5,960,056 A | | 9/1999 | Lai | |
| 6,075,836 A | * | 6/2000 | Ning | ....................... 378/98.12 |
| 6,078,638 A | * | 6/2000 | Sauer et al. | .................... 378/4 |

OTHER PUBLICATIONS

L.A. Feldkamp, L.C. Davis, and J.W. Kress, Practical cone-beam algorithm, J. Opt. Soc. Am., vol. 1(A) 612–619, 1984.
K. Taguchi and H. Aradate, Algorithm for image reconstruction in multi–slice helical CT, Med Phys. 550–561 Apr. 1998.
H. Hu, Multi–slice helical CT: Scan and reconstruction, Med.Phys. 26(1) Jan. 1999 pp 5–18.
G. Wang et al, A General Cone–Beam Reconstruction Algorithm, IEEE Trans. on Medical Imaging, vol. 12, No. 3, 486–496 Sep. 1993.
S. Schaller, T. Flohr, and P. Steffen, A New Approximate Algorithm for Image Reconstruction in Cone–Beam Spiral CT at Small Cone–Angles, IEEE Nuclear Science Symp. Record Conf. (Anaheim, CA 1996) vol. 3 ed. A. DelGuerra 1703–9.
D.L. Parker, Optimal short scan convolutional reconstruction for fanbeam CT, Med. Phys. 9(2), Mar. 1982 pp 254–257.
D.L. Parker, Optimization of Short Scan Convolutional Reconstruction in Fan Beam CT, IEEE pp. 199–202.
G. Besson, New classes of helical weighting algorithms with applications to fast CT reconstruction, Med. Phys. 25(8), Aug. 1998 pp. 1521–1532.
G. Besson, CT fan–beam parameterizations leading to shift-invariant filtering, Inverse Probl. 12, 815–833, 1996.

* cited by examiner

*Primary Examiner*—David V. Bruce
(74) *Attorney, Agent, or Firm*—Carl B. Horton, Esq.; Armstrong Teasdale LLP

(57) ABSTRACT

The present invention is, in one embodiment, a method for multi-slice, computed tomography imaging. The method includes steps of moving an x-ray source through a trajectory; projecting an x-ray cone beam from the moving x-ray source through an object towards a curved detector; and determining contributions of segments along the trajectory to voxels in a reconstruction volume of the object, including compensating the determined contributions for curvature of the detector and x-ray cone beam geometry.

32 Claims, 4 Drawing Sheets

METHODS AND APPARATUS FOR CONE BEAM MULTISLICE CT CORRECTION

BACKGROUND OF THE INVENTION

This invention relates generally to methods and apparatus for reconstruction of imaging data, and more particularly to cone beam correction for reconstruction of three-dimensional computed tomography imaging data.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

In at least one known multi-slice CT system, a "cone angle," or volumetric content of measured data, is very small. Therefore, this system currently processes 3-dimensional data using a 2-dimensional algorithm. By using the Feldkamp (FDK) algorithm, which is a simple perturbation of a 2-dimensional filtered backprojection (FBP) algorithm for image reconstruction, excellent image quality is obtained for these relatively small cone angles. The FDK algorithm is not exact, however, and as the number of slices increases (for fixed slice thickness) cone angle and cone beam artifacts increase.

It would be desirable to extend 2-dimensional CT fan-beam reconstruction algorithms to the cone-beam geometry of a third-generation multi-slice CT imaging system. Such a reconstruction could be based upon a modified FDK algorithm, but the modifications would have to compensate for both a cylindrical (rather than planar) area detector, and a helical (rather than circular) source trajectory. Use of a curved detector array requires data interpolation along curved lines on the detector, the application of a new data filter, and of pre- and post-convolution weights. However, the helical source trajectory complicates voxel-driven back-projection in that variable data (projection ray) redundancy conditions are encountered across a reconstructed image. For each voxel in a reconstruction volume, it is necessary to compute, for each source position, a ray passing from the x-ray source through the voxel. Thus, approaches must be found to address the handling of data redundancy and handling the variable number of rays that contribute to voxels.

Two approaches to addressing the problems of data redundancy and the variable number of rays contributing to voxels are known. In one approach, the helical pitch is limited so that at least two (interpolated) samples are obtained for each voxel. Extra data is thrown away, retaining only $2\pi$ worth of projections. The z-resolution available from conjugate rays is ignored to keep the approach simple. However, in patient scanning, this approach is impractical, because it severely limits patient coverage and results in increases radiation dose. A second approach improves on the first by providing better image quality (IQ) and reduced patient dose, while handling any practical pitch. However, a method implementing this approach to handling the above-mentioned problems requires that all data passing through a given voxel (for given source and fan angles) are simultaneously available. As a result, methods based on the second approach are impractical to implement.

It would therefore be desirable to provide methods and apparatus that provide acceptable compromises between improved image quality and practicality in third generation CT imaging systems.

BRIEF SUMMARY OF THE INVENTION

There is therefore provided, in one embodiment, a method for multi-slice, computed tomography imaging. The method includes steps of moving an x-ray source through a trajectory; projecting an x-ray cone beam from the moving x-ray source through an object towards a curved detector; and determining contributions of segments along the trajectory to voxels in a reconstruction volume of the object, including compensating the determined contributions for curvature of the detector and x-ray cone beam geometry.

The above described embodiment and others described in detail herein provide improved image quality in third generation CT imaging systems, even for cylindrical detectors and helical source trajectories. In addition, these embodiments can be implemented within the practicality constraints imposed by CT imaging hardware and patient dosage limitations.

DETAILED DESCRIPTION OF THE INVENTION

Figure 1:
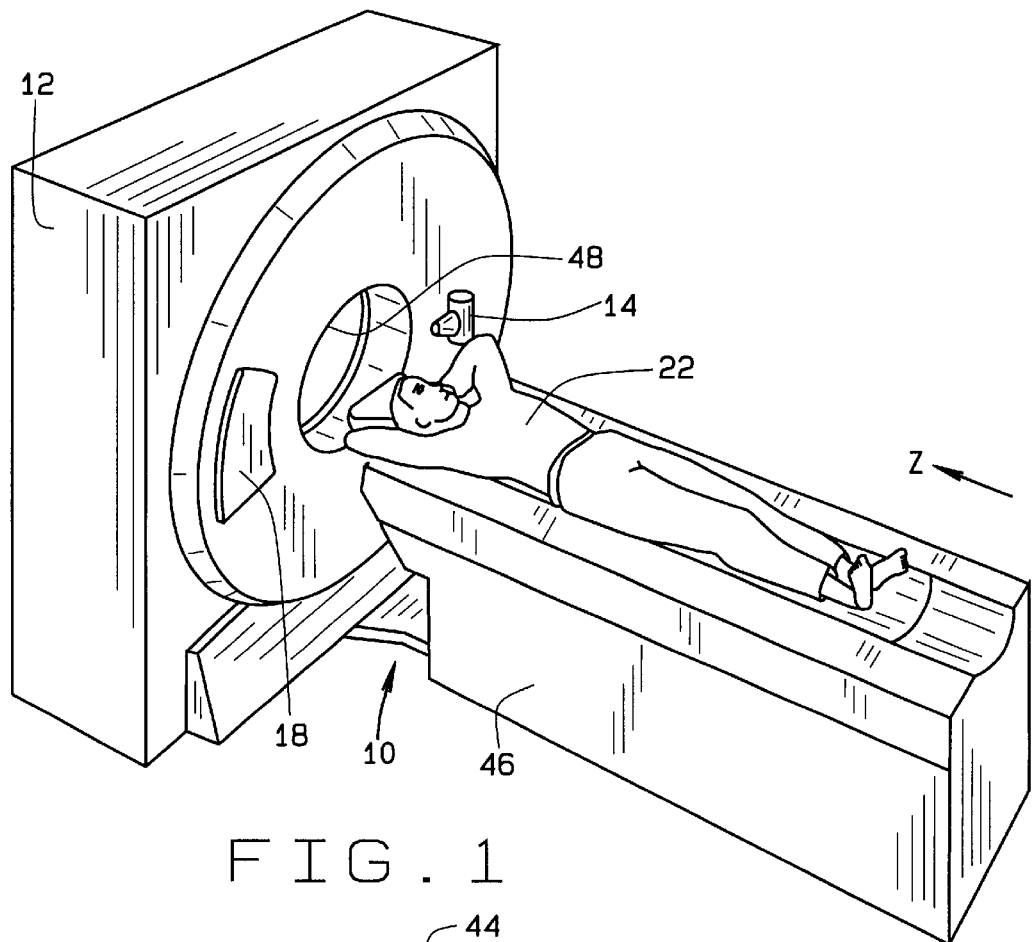
FIG. 1 is a pictorial view of a CT imaging system.
Figure 2:
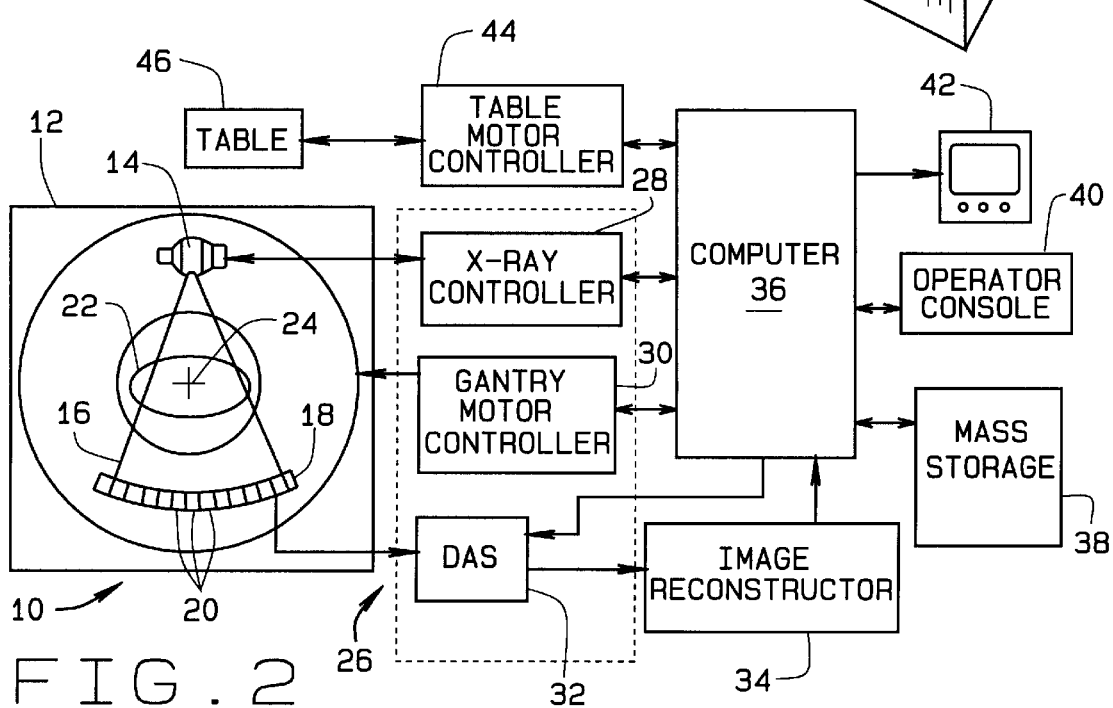
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
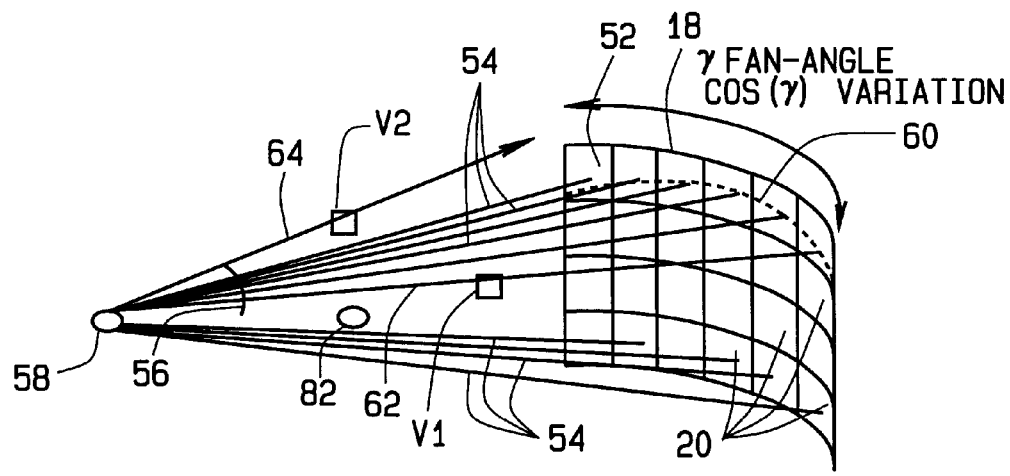
FIG. 3 is a geometric representation of an embodiment of a third generation, four slice CT imaging system.

In one embodiment of the present invention, a 2-dimensional CT fan-beam reconstruction method is extended to a cone-beam geometry on a third generation multi-slice CT. A curved, cylindrical detector is used rather than a planar area detector, as is a helical, rather than a circular, source trajectory. The curved detector array produces data that is interpolated along curved lines of the detector by subsequent processing, and a data filter is used to filter the interpolated data using pre- and post-convolution weights. The helical source trajectory produces variable data (projection ray) redundancy conditions across the reconstructed image of the voxel-driven backprojection. Therefore, for each view in the reconstruction volume, a ray passing from the x-ray source through each voxel is computed. The geometry of an embodiment of a third generation, four-slice system is shown schematically in FIG. 3. Gantry 12 rotates about a z-axis 50. Detector 18 surface 52 lies on a cylinder, with four rows, each having 888 detector elements 20. Row data represent rays 54 that do not lie in horizontal reconstruction planes. A "cone angle" 56 with respect to a gantry plane (which itself is defined as a plane orthogonal to a z-axis that contains the source 14 point and bisects the detector 18 cylinder) represents a degree of inconsistency in cone beam data as compared to two-dimensional CT data. Planes containing a focal spot or point 58 intersect detector surface 52 along arcs 60 that drop off as $\cos(\gamma)$. A ray 62 that passes through voxel V1 hits detector array 18, so that data representing voxel V1 is estimated by interpolation. A ray 64 through voxel V2, however, does not hit detector array 18, so data representing voxel V2 is estimated by extrapolation.

In one embodiment, a compromise is effected between improved image quality and practicality by combining voxel-driven backprojection, data extrapolation, and weighting methods, such as half-scan, underscan, and overscan, to handle data redundancy conditions and smooth out discontinuities at the 0, $2\pi$ source angle interface for helical trajectories. Use of extrapolation allows high scanning pitches to be used by providing a constant number of projection measurements for all voxels for a given source position and by ensuring that no measurement is discarded. Extrapolation thus eliminates cone-angle and detector size-related variable voxel sampling of source positions. Source-related data redundancies and associated vanishing weights (half-scan weights in high speed (HS) pitches, overscan or underscan in high quality (HQ) pitches) are used to manage data inconsistencies resulting from the combination of cone-angle and helical scanning. To enable independent projection processing, HS and HQ pitches are calculated such that at least one ray or two rays, respectively, contribute to a given voxel.

Figure 4:
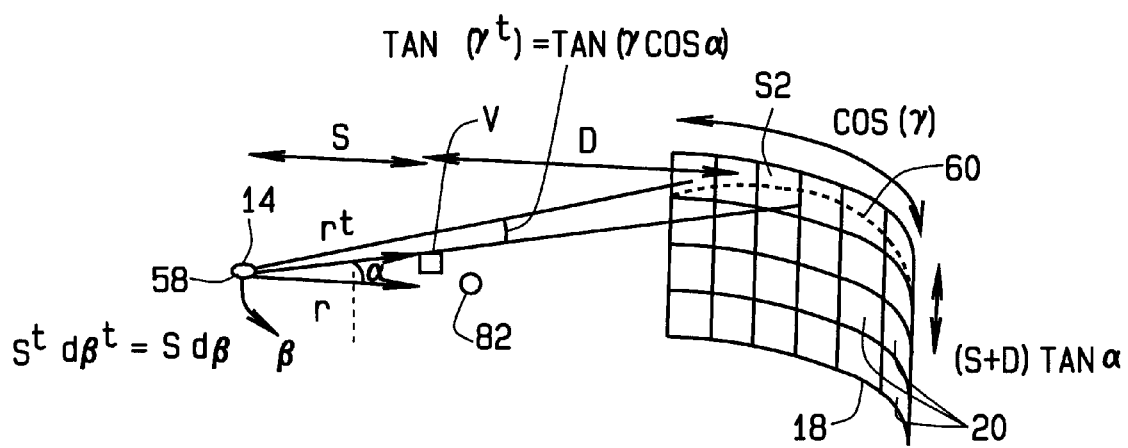
FIG. 4 is a geometric diagram showing conversion of FDK infinitesimals into third generation geometry.

In one embodiment, a Feldkamp (FDK) reconstruction algorithm is modified for use in third-generation multi-slice CT imaging systems. FDK is a perturbation of 2-dimensional filtered backprojection (FBP), which calculates a double integral over a fan angle, $\gamma$, and a source angle, $\beta$, for each point in a reconstructed image. In FDK, a contribution of each infinitesimal segment along a source trajectory to a voxel in a reconstruction volume is computed as if the segment were contributing to the 2-dimensional reconstruction in a plane defined by the infinitesimal segment and the point/voxel. Therefore, FDK is derived from 2-dimensional FBP by a change of variables. Referring to FIG. 4 and voxel V, S is a source 14 to isocenter 82 distance; S+D is a source 14 to detector 18 distance; $\beta$ is a source angle, $\beta^t$ is a source angle in a tilted plane; $\gamma$ is a fan angle; $\gamma^t$ is a fan angle in the tilted plane; and $\alpha$ is an angle between a horizontal and a tilted plane. $\vec{r}$ is a radial vector, and $\vec{r}^t$ is a radial vector in the tilted plane under consideration (i.e., tilted with respect to the gantry plane.) Embodiments in which flat panel x-ray detectors are used do not require interpolation onto $\cos(\gamma)$ arcs; i.e., filtering along detector rows is equivalent to filtering co-planar data for such panels. Therefore, the changes of variables differ somewhat in embodiments using a flat panel x-ray detector.

After interpolating projection data onto planar sets, projection rays are distributed within the fan according to a fan-beam parameterization written as:

$$S^t \, d\beta^t = S \, d\beta$$

$$\tan \gamma^t = \tan \gamma \cos \alpha \quad (1)$$

where $\gamma^t$ represents the fan angle in the tilted plane, and $d\beta^t$ represents the infinitesimal arc length in the tilted plane indicated by $\vec{r}^t$ as shown in FIG. 4. Thus.

$$\cos\gamma^t \, d\gamma^t = \frac{\cos\alpha \, d\gamma}{(\cos^2\gamma + \cos^2\alpha \, \cos^2\gamma)^{3/2}} \quad (2)$$

Plugging (1) and (2) into the 2-dimensional FBP reconstruction formula thus results in an embodiment that exactly implements FDK on a third generation CT imaging system.

An approximation leads to an embodiment of a shift-invariant filter that very closely approximates the true, shift-variant filter, but which is simpler and more readily accommodates convolution in the Fourier domain. One embodiment of a reconstruction algorithm of the present invention utilizing an exact shift-variant filter for FDK and its shift-invariant approximation is described as follows.

A third-generation FDK fan-beam parameterization in tilted planes is given by (3):

$$\eta(\gamma^t) = \arctan[(\cos \alpha) \times \tan(\gamma^t)]. \tag{3}$$

A shift-invariant approximation to a shift-variant kernel (written omitting the superscript t) is written:

$$\sin[\eta(\gamma) - \eta(\tilde{\gamma})] \approx \left[\frac{\eta'(\gamma)\eta'(\tilde{\gamma})}{\eta'(0)\eta(\gamma - \tilde{\gamma})}\right]^{1/2} \sin[\eta(\gamma - \tilde{\gamma})]. \tag{4}$$

Accordingly, the following equation is written by substituting for $\eta$ in equation (4) above:

$$g(\gamma - \tilde{\gamma}) = \left(\frac{\gamma - \tilde{\gamma}}{\sin(\eta(\gamma) - \eta(\tilde{\gamma}))}\right)^2 h(\gamma - \tilde{\gamma}) \approx A(\gamma) K(\gamma - \tilde{\gamma}) h(\gamma - \tilde{\gamma}) B(\tilde{\gamma}) \tag{5}$$

where h( ) is a parallel kernel and A, B, and K are written as:

pre-convolution weight:

$$A(\gamma) = 1 + \cos^2\alpha \, \tan^2\gamma / 1 + \tan^2\gamma; \tag{5a}$$

post-convolution weight:

$$B(\gamma) = 1 + \cos^2\alpha \, \tan^2\tilde{\gamma} / 1 + \tan^2\gamma; \tag{5b}$$

The kernel terms that multiply the expression for the parallel kernel h are written as:

$$K(\gamma - \tilde{\gamma}) = \frac{1 + \tan^2(\gamma - \tilde{\gamma})}{1 + \cos^2\alpha \tan^2(\gamma - \tilde{\gamma})} \times \left(\frac{\gamma - \tilde{\gamma}}{\sin\{\arctan[\cos\alpha\tan(\gamma - \tilde{\gamma})]\}}\right)^2 \tag{6}$$

By replacing the shift-variant kernel g by the shift-invariant approximation above into equation (8), an exact third-generation FDK algorithm embodiment is obtained.

In another embodiment useful for small cone-angles, such as those associated with current multi-slice scanners, an approximation that directly renders the filtering shift-invariant (and therefore enables convolution) is utilized. This embodiment is useful for high speed mode. For small angles, the convolution is simplified by approximating fan-beam parameterization by:

$$\gamma^t = \gamma \cos \alpha \tag{7}$$

where $\alpha = \alpha(v, \beta)$. The reconstruction algorithm is then written as:

$$f(v) = \int_0^{2\pi} \frac{S}{L^2(v, \beta)} [g \otimes p^*](\gamma; \xi', \beta) \frac{\cos^{3/2}(\gamma \cos \alpha) d\beta}{(\cos^2\gamma + \sin^2\gamma \cos^2\alpha)^{3/2}}, \tag{8}$$

or, in a half-scan weighted embodiment, $$f(v) = \int_0^{\pi+2\Gamma} \frac{S}{L^2(v, \beta)} [g \otimes (p^* \times HSW(\beta, \gamma))] \tag{9}$$

$$(\gamma; \xi', \beta) \frac{\cos^{3/2}(\gamma \cos \alpha) d\beta}{(\cos^2\gamma + \sin^2\gamma \cos^2\alpha)^{3/2}}$$

where:
$\otimes$ represents convolution;
$\Gamma$ is a maximum fan angle of the fan beam;
S is a source to isocenter distance;
v is a voxel with cylindrical coordinates (r, $\psi$,$\kappa$);
$\xi' = \xi'$ (v,$\beta$) is a z-elevation for a projection of v onto a detector;
L is a voxel to source distance (in three-dimensional space);
g( ) denotes a fan-beam reconstruction convolution kernel;
P* is data that has been interpolated onto a tilted plane; and
HSW denotes the half-scan weights.

To process image data in accordance with equation (9), x-ray source 14 is moved through a trajectory, and a cone beam 16 is projected from x-ray source 14 through an object or patient 22 towards curved detector 18. A signal representative of detected x-rays 16 passing through object 22 is processed by imaging system 10, for example, by DAS 32, imaging reconstructor 34, and computer 36, to produce a tomographic image that appears on CRT display 42. (As used herein, the "signal representative of detected x-rays" is intended to be broadly construed. For example, embodiments in which parallel data lines for detector elements 20 are used to transmit the signal from detector 18 to DAS 32 are intended to be included, as are embodiments which multiplex data on a single line.) The processing of the signal in accordance with equation 9 comprises applying half scan weights to pre-processed data, prior to reconstruction filtering. These weights account for the fact that several line integrals have been measured twice, while most have been measured only once. Next, reconstruction filtering is performed, as represented by the convolution of g and p×HSW in equation 9. Next, backprojection is applied in three-dimensional space, with compensation for x-ray cone beam geometry, by summing contributions from each projection to a given pixel. This backprojection is represented by the integral sum in equation 9.

In an embodiment useful for high quality modes, interpolation of projection data along cos($\gamma$) arcs is eliminated. Accordingly, projection data are filtered along detector rows. The parameterization approximation (8) is retained.

Figure 5:
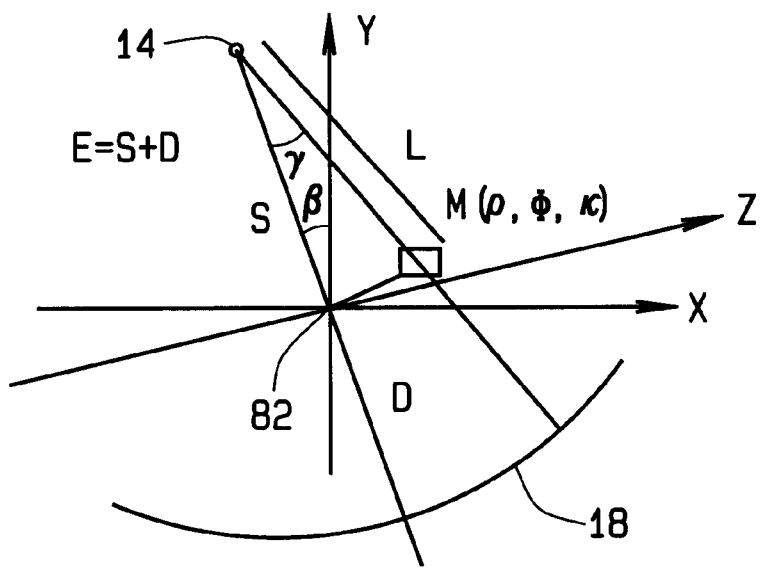
FIG. 5 is a geometric representation of fan beam geometry.

A derivation of one embodiment of an FDK algorithm of the present invention approximating FDK for third generation CT imaging systems 10 without cos($\gamma$) detector interpolation involves two approximations. The approximations are first, that the cone angle is small, so that convolution filtering is possible, and second, that the data are filtered along detector rows (i.e., without interpolation along cos($\gamma$) arcs). FIG. 5 is a geometric representation of fan-beam geometry. All angles and distances refer to a central plane of gantry 12, orthogonal to a z-axis. A voxel M is shown projected onto the gantry 12 central plane. Considering reconstruction of voxel M with a multi-slice detector 18, a change of geometry from fan-beam to cone-beam results in a source to isocenter distance S changing into a source to z-axis $S^t$ given by:

$$S^t = [S^2 + \xi^2]^{1/2},$$

where $\xi$ is measured on the z-axis, and the source to detector distance E=S+D (as measured on a ray through the z-axis) is changed into $E^t$, given by:

$$E^{t2}[E^2+\xi^2],$$

where $\xi$ is measured on detector 18.

Starting from a 2D reconstruction equation for fan-beam data, and in the notation of FIG. 5:

$$f(r,\phi) = \int_0^{2\pi} \frac{S}{L^2} \int_{-\Gamma}^{\Gamma} p^*(\beta,\gamma) g(\gamma-\tilde{\gamma})\cos\gamma\, d\gamma\, d\beta \quad (10)$$

with:

$$g(u) = \frac{1}{2}\left(\frac{u}{\sin u}\right)^2 h(u),$$

where h(u) denotes a parallel-geometry kernel.

Using a multi-slice detector, the geometry changes from fan-beam to cone-beam in reconstruction of a voxel M. As a result, a source to isocenter distance S is changed into the source to z-axis distance $S^t$ written as:

$$S^t = [S^2+\xi^2]^{1/2},$$

where $\xi$ is measured on the z-axis.

Also, the source to detector distance (as measured on a ray through the z-axis), is changed from E to $E^t$ written as:

$$E^{t2} = [E^2+\xi^2],$$

where $\xi'$ is measured on the detector.

Figure 6:
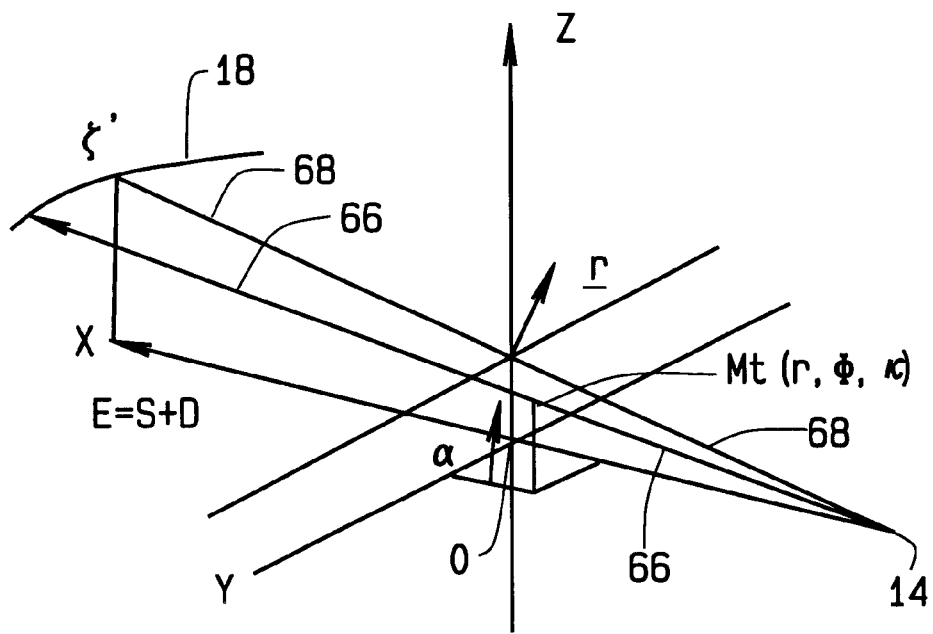
FIG. 6 is a geometric representation of a third generation, cone-beam geometry with a cylindrical detector.

FIG. 6 is a geometric representation of a third-generation, cone-beam geometry with a cylindrical detector 18. A ray 66 with a cone-angle α with respect to a plane of gantry 12 is shown, the plane being defined by O, x, and y in FIG. 6. Also shown is an associated ray 68 (for the same elevation on detector 18) passing through an axis of rotation z. A rotation angle $d\beta^t$ such that a small rotation dβ around z is equivalent to $d\beta^t$ around r is written as:

$$d\beta^t = \frac{S}{\sqrt{S^2+\xi^2}}\, d\beta. \quad (11)$$

A fan-angle γ in a plane of the gantry (orthogonal to z) is now replaced by a fan-angle $\gamma^t$ in a tilted surface:

$$\gamma' = \frac{E}{E'}\gamma = \gamma\cos(\alpha),$$

(exactly under the assumptions above).

Accordingly:

$$g(\gamma'-\tilde{\gamma}') = \left(\frac{E^t}{E}\right)^2 g(\gamma-\tilde{\gamma}). \quad (12)$$

Voxel-dependent geometric weight factor is determined. As data are filtered along detector rows, for a given voxel M, an associated $\xi$ to be used in the calculation of $d\beta'$ above is found. Given $\xi'=(E/L)\kappa$, and $\xi=(S/E)\xi'$, it is thus written:

$$\xi = \frac{S}{L}\kappa. \quad (13)$$

Putting all the terms together, an equation for a third-generation FDK reconstruction algorithm is written:

$$f(r,\phi,\kappa) = \int_0^{2\pi}\int_{-\Gamma}^{\Gamma} \frac{S}{L^2+\kappa^2}\frac{E'}{E} g(\gamma-\tilde{\gamma}) p^*(\beta,\gamma,\xi')\cos\left(\frac{E}{E'}\gamma\right) d\gamma\, d\beta \quad (14)$$

Alternatively, an equation for an embodiment of a modified FDK algorithm is written as:

$$f(r,\phi,\kappa) = \quad (15)$$

$$\int_0^{2\pi}\int_{-\Gamma}^{\Gamma} \frac{S}{L^2+\kappa^2}\frac{1}{\cos(\alpha)} g(\gamma-\tilde{\gamma})p^*(\beta,\gamma,\xi')\cos(\gamma\cos(\alpha))d\gamma\, d\beta,$$

or, in an overscan or underscan weighted embodiment, $$f(r,\phi,\kappa) = \int_0^{2\pi+B}\int_{-\Gamma}^{\Gamma} \frac{S}{L^2+\kappa^2}\frac{1\times SW(\beta,\gamma)}{\cos(\alpha)} \quad (16)$$

$$g(\gamma-\tilde{\gamma})p^*(\beta,\gamma,\xi')\cos(\gamma\cos(\alpha))d\gamma\, d\beta$$

where B denotes the overscan angle, and SW(β,γ) denotes a weight function that is either an overscan weight function or an undersean weight function. (For underscan, B=0).

To process image data in accordance with equation (16), x-ray source 14 is moved through a trajectory. A cone beam 16 is projected from x-ray source 14 through an object or patient 22 towards curved detector 18. A signal representative of detected x-rays 16 passing through object 22 is processed by imaging system 10 by, for example, DAS 32, imaging reconstructor 34, and computer 32, to produce a tomographic image that is displayed on CRT display 42. The processing of the signal in accordance with equation (16), when SW(β,γ) is an underscan weighting function, comprises weighting, filtering, and backprojecting the data, in that order. Backprojection is performed in three-dimensional space, with compensation for x-ray cone beam geometry. When SW(β,γ) is an overscan weighting function, the weights depend only upon a source angle. In this case, the weights account for the fact that projection data have been acquired over a range of source angles larger than 2π, and accordingly, several line integrals have been measured three times. Thus, filtering is performed before weighting, and weighting is performed before backprojecting.

In one embodiment, an FDK algorithm is adapted to helical trajectories. In known multi-slice CT systems, most imaging is helical. Helical scanning is possible by using a modification in which all z distances are calculated with respect to a gantry central plane. However, appropriate attention must be given to obtaining an appropriate number of data samples for each voxel in the reconstructed image and handling of data redundancy. Providing at least two samples from the detector using only interpolation leads to very slow pitch and 2 to 3 samples per voxel; on the other hand, handling sampling discrepancy by simply throwing away a third sample is not acceptable from a patient dose standpoint. Therefore, in one embodiment, extrapolation is used to enable faster pitches while taking into account all projection samples. Standard weighting techniques are used to handle data redundancy. Specifically, a HQ mode utilizing this embodiment accounts for two or more samples per voxel. Data redundancy from a third sample is handled by employing overscan or underscan weights to smooth away data discrepancies resulting from the helical trajectory. In an HS mode embodiment, one or two samples per voxel are used. Data redundancies associated with the second sample are handled using half-scan weights to feather data inconsistencies resulting from the helical trajectory and cone-angle.

In one embodiment, for an eight-slice system, a 7:1 pitch is used to provide a best cone-artifact abatement measure. A modified FDK algorithm given by equation (15) is used with an additional modification making the gantry plane source-angle dependent. Also, the backprojection was extended from $2\pi$ to $(8/7+\epsilon) \times 2\pi$ using overscan weights, where $\epsilon$ is a parameter of the method. The use of overscan weights avoids data inconsistencies of helical algorithm implementations at source angles 0 and $2\pi$ relating to a z-motion of the patient with respect to the source. (Imaging without handling this inconsistency results in streak artifacts in a direction of the source position at angle 0.) Useful overscan functions include those written as:

$$f(x)=3x^2-2x^3,$$

where x varies between 0 and 1 in the interval considered;

$$f(x) = \frac{\left|\sin(\frac{\pi}{2}(1+x))\right|^\delta}{\left|\cos\left[\frac{\pi}{2}(1+x)\right]\right|^\delta + \left|\sin\left[\frac{\pi}{2}(1+x)\right]\right|^\delta},$$

where x varies between 0 and 1 in the interval considered, and $\delta$ is a parameter.

In one embodiment, high pitch reconstructions are implemented by applying ½ scan weights to the modified FDK algorithm described above, equation (8). In another embodiment, the data are backprojected on a three-dimensional Cartesian grid.

In one embodiment of the present invention, x-ray source 14 is moved through a helical trajectory relative to object 22. An x-ray cone beam 16 is projected from source 14 through object 22 to a curved, cylindrical detector 18. Processing of detector data to produce CT images in imaging system 10 is provided by DAS 32, imaging reconstructor 34, and computer 36, for example, and an image is displayed on CRT display 42. This processing includes determining contributions of segments along the trajectory to voxels in a reconstruction volume of the object, including compensating the determined contributions for curvature of the detector and x-ray cone beam geometry. This determination comprises filtering and backprojecting using a double integral over a fan angle and source angle for each point in the reconstruction volume.

Figure 7:
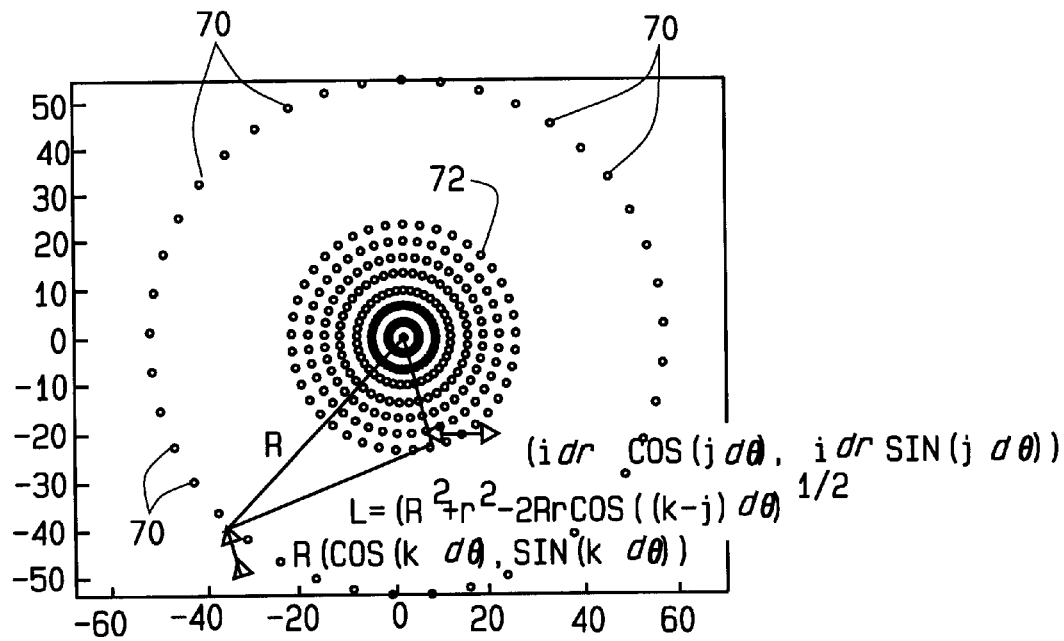
FIG. 7 is a graphical representation of a polar reconstruction lattice.

Referring to the graphical representation of a polar reconstruction lattice shown in FIG. 7, an exemplary embodiment of the present invention was implemented using a reconstruction done on a polar lattice using MATLAB. The dimensions of the axes of FIG. 7 are in cm. for the exemplary embodiment. Forty-one of 984 source positions 70 are shown. An undersampled reconstruction lattice 72 is also shown. The image was interpolated onto a Cartesian lattice using MATLAB's cubic interpolation call. A polar lattice is an appropriate geometry for a third generation system having a circular source trajectory. An angular lattice increment equal to the angular increment of CT scanner 10 between views was selected, $d\theta d\beta = 2\pi/N_{views}$, so that $dr \sim dx$, where dx a distance between reconstruction lattice points is roughly dx at outer edges of the FOV, decreasing to zero at the center. The polar lattice simplified programming, and further permitted precomputation of all trigonometric functions used in the backprojection.

Figure 8:
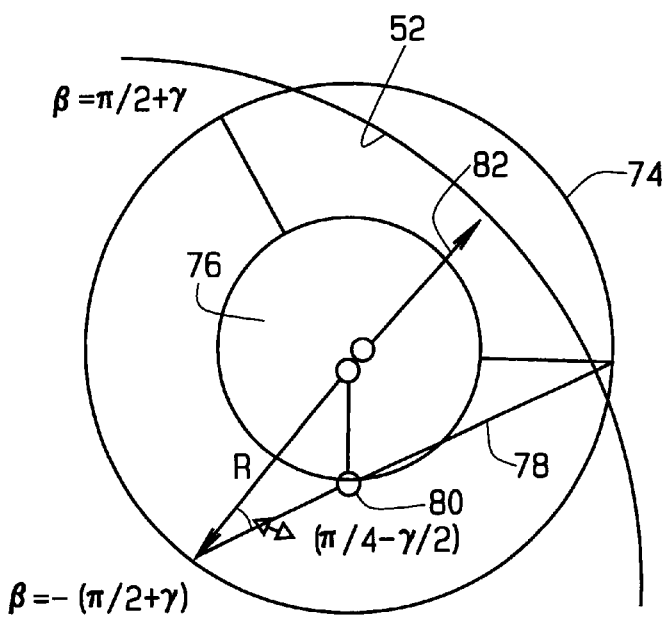
FIG. 8 is a geometric representation of a third generation geometry and source trajectory.

In FIG. 7, R is a source trajectory radius and $kd\theta$ represents a source angle. A pixel under consideration is at a radial distance r and an angle $jd\theta$. With this in mind, it is relatively simple to compute L, a source-pixel distance. The only trigonometric functions needed to calculate these distances L are $\{\cos(i\ d\theta)\}$ for $i=0, \ldots$ (number of views $-1$). An extension to a 3d backprojection is also simple, and is given by $L_{3d}(L^2+dz^2)^{\frac{1}{2}}$. Precomputation significantly reduced the algorithm's floating point operation (FLOP) count, and efficiency could also be improved by avoiding backprojection onto every lattice point near the origin. (Selective backprojection onto some points in the polar lattice increases the programming burden.) Referring to the geometric representation of third generation and source trajectory shown in FIG. 8, $0^{th}$ order extrapolation was used when the required data in the voxel-driven backprojection fell above or below the 8-slice detector. First order or higher order, or non-polynomial methods, might be used for the extrapolation. A source trajectory 74 and detector surface 52 are shown. A region of reconstruction is shown at 76. Half-scan data was collected only between view angles $-(\pi/2+\Gamma)$ and $+(\pi/2+\Gamma)$. A ray 78 through a point 80 at view angle $-(\pi/2+\Gamma)$ does not hit detector 18 surface 52 for helical pitches above $N_{slices}/2$, and hence, data for ray 78 is extrapolated. However, a conjugate ray 82, collected a view angle 0, is always measured by detector 18 with cone angle=0. In one embodiment illustrated in FIG. 8, R=54.1 cm; D=40.8 cm; FOV=48 cm; $\Gamma=27.4°$; $z_{source}$=pitch×slice width×$(\pi/2+\gamma)/(2\pi)$; and $\kappa$=ray height on detector=$-z_{source} \times (R+D)/L \sim 1.06 \times$ pitch×slice width.

From the preceding description of various embodiments of the present invention, it is evident that the embodiments described herein lead to simple changes in data processing that makes reconstruction more robust to large cone angles. Data are filtered "on the fly," with only minor changes to standard reconstruction chains. The embodiments described herein should be contrasted with previously known adaptations of the FDK algorithm to third-generation CT with cylindrical detectors that fail to account for geometry and thus filter non-coplanar data. In addition, the embodiments described herein do not require simultaneous data availability for all rays passing through a voxel for a given 2D Radon point as does at least one other known reconstruction method. The embodiments described herein also fully use patient dose while providing increased patient coverage. Artifacts are effectively eliminated by the use of over-scan weights or underscan weights (respectively half-scan weights), which, in combination with the use of extrapolation, makes the use of high pitches practical in all imaging modes without wasting patient dose. The embodiments described herein use relatively few views as compared to at least one previously known four slice helical reconstruction algorithm, and accordingly lead to fast reconstruction and improved temporal resolution. It will be recognized by those skilled in the art that the method and apparatus embodiments of the present invention described herein provide acceptable compromises between improved image quality and practicality in third generation CT imaging systems. Moreover, these embodiments can be implemented within the practicality constraints imposed by CT imaging hardware and patient dosage limitations.

Although particular embodiments of the invention have been described and illustrated in detail, it is to be clearly understood that the same is intended by way of illustration and example only and is not to be taken by way of limitation.

For example, embodiments of the invention are applicable to 8, 16, or other numbers of detector rows. Also, the embodiments described herein use detector row-to-row interpolation for a given source position. However, further improvement in image quality at small cone angles can be obtained, with somewhat increased implementation complexity, by using conjugate ray interpolation/extrapolation to zero-cone angle. In addition, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used if individual detector elements are corrected to provide substantially uniform responses to a given x-ray beam. Accordingly, the spirit and scope of the invention are to be limited only by the terms of the appended claims and legal equivalents.

What is claimed is:

1. A method for multi-slice, computed tomography imaging, said method comprising:
   moving an x-ray source through a trajectory;
   projecting an x-ray cone beam from the moving x-ray source through an object towards a curved detector; and
   determining contributions of segments along the trajectory to voxels in a reconstruction volume of the object, including compensating the determined contributions for curvature of the detector and x-ray cone beam geometry.

2. A method in accordance with claim 1 and further wherein determining contributions of segments along the trajectory to voxels in a reconstruction volume of the object comprises the step of filtering and backprojecting using a double integral over a fan angle and source angle for each point in the reconstruction volume.

3. A method in accordance with claim 2 wherein backprojecting using a double integral comprises backprojecting onto a polar reconstruction lattice.

4. A method in accordance with claim 1, wherein the curved detector is a cylindrical detector, and compensating the determined contributions for curvature of the detector and x-ray cone beam geometry comprises the step of compensating the determined contributions for curvature of the cylindrical detector.

5. A method in accordance with claim 1, wherein moving an x-ray source through a trajectory comprising moving the x-ray source through a helical trajectory relative to the object.

6. A method for multi-slice, computed tomographic imaging, said method comprising:
   moving an x-ray source through a trajectory;
   projecting an x-ray cone beam from the moving x-ray source through an object towards a curved detector; and
   weighting, filtering, and backprojecting a signal representative of detected x-rays passing through the object to produce a tomographic image, wherein backprojecting using a signal representative of detected x-rays comprises backprojecting onto a polar reconstruction lattice;
   the backprojection being performed in a three-dimensional space, with compensation for x-ray cone-beam geometry.

7. A method in accordance with claim 6, wherein said weighting is performed prior to said filtering, and said filtering is performed prior to said backprojecting.

8. A method in accordance with claim 6, wherein said weighting is performed prior to said filtering, and said filtering is performed prior to said backprojection.

9. A method in accordance with claim 8, wherein weighting, filtering, and backprojecting a signal representative of detected x-rays passing through the object to produce a tomographic image comprises determining a reconstruction image function $f(v)$ written as:

$$f(v) = \int_0^{\pi+2\Gamma} \frac{S}{L^2(v,\beta)} [g \otimes (p^* \times HSW(\beta, \gamma))]$$

$$(\gamma; \xi', \beta) \frac{\cos^{3/2}(\gamma \cos \alpha) d\beta}{(\cos^2\gamma + \sin^2\gamma \cos^2 \alpha)^{3/2}}$$

where:
  $\otimes$ represents convolution;
  S is a source to isocenter distance;
  v is a voxel with cylindrical coordinates (r, $\psi$, $\kappa$);
  $\xi' = \xi'(v,\beta)$ is a z-elevation for a projection of v onto a detector;
  L is a voxel to source distance (in three-dimensional space);
  g( ) denotes a fan-beam reconstruction convolution kernel;
  p* is data that has been interpolated onto a tilted plane;
  HSW( ) denotes the half-scan weights;
  $\gamma$ is a fan angle;
  $\beta$ is a source angle;
  $\alpha$ is an angle between a horizontal plane and the tilted planes; and
  $\Gamma$ is a maximum fan angle of the fan beam.

10. A method in accordance with claim 9 wherein $$g(\gamma - \tilde{\gamma}) = \left(\frac{\gamma - \tilde{\gamma}}{\sin(\eta(\gamma) - \eta(\tilde{\gamma}))}\right)^2 h(\gamma - \tilde{\gamma}) \approx A(\gamma) K(\gamma - \tilde{\gamma}) h(\gamma - \tilde{\gamma}) B(\tilde{\gamma});$$

where h( ) is a parallel kernel and A, B, and K are written as:

$$A(\gamma) = \frac{1 + \cos^2\alpha \tan^2\gamma}{1 + \tan^2\gamma};$$

$$B(\tilde{\gamma}) = \frac{1 + \cos^2\alpha \tan^2\tilde{\gamma}}{1 + \tan^2\tilde{\gamma}};$$

$$K(\gamma - \tilde{\gamma}) = \frac{1 + \tan^2(\gamma - \tilde{\gamma})}{1 + \cos^2\alpha \tan^2(\gamma - \tilde{\gamma})} \times \left(\frac{\gamma - \tilde{\gamma}}{\sin\{\operatorname{atan}[\cos\alpha \tan(\gamma - \tilde{\gamma})]\}}\right)^2;$$

and $$\eta(\gamma) = \arctan[(\cos \alpha) \times \tan(\gamma)];$$

and where $\gamma$ is a fan angle for a ray passing through a voxel being reconstructed.

11. A method in accordance with claim 7 wherein moving the x-ray source through a trajectory comprises the step of moving the x-ray source in a helical trajectory relative to the object.

12. A method in accordance with claim 7 wherein projecting an x-ray cone beam from the moving x-ray source through an object towards a curved detector comprises the step of projecting the x-ray cone beam from the moving x-ray source through an object towards a cylindrical detector.

13. A method in accordance with claim 6, wherein weighting, filtering, and backprojecting a signal representative of detected x-rays passing through the object to produce a tomographic image comprises determining a reconstruction image function $f(v)=f(r, \phi, \kappa)$ written as:

$$f(r, \phi, \kappa) = \int_0^{2\pi+B\Gamma} \int_{-\Gamma}^{\Gamma} \frac{S}{L^2+\kappa^2} \frac{l \times SW(\beta, \gamma)}{\cos(\alpha)} g(\gamma - \tilde{\gamma}) p^*(\beta, \gamma, \xi') \cos(\gamma \cos(\alpha)) d\gamma d\beta$$

where:
B denotes an overscan angle;
SW($\beta,\gamma$) denotes a member of a group consisting of overscan and underscan weight functions;
S is a source to isocenter distance;
v is a voxel with cylindrical coordinates (r, $\psi,\kappa$);
$\xi'=\xi'$ (v,$\beta$) is a z-elevation for a projection of v onto a detector;
L is a voxel to source distance (in three-dimensional space);
g( ) denotes a fan-beam reconstruction convolution kernel;
p* is data that has been interpolated onto a tilted plane;
$\gamma$ is a fan angle;
$\gamma$ is a fan angle for a ray passing through a voxel being reconstructed;
$\beta$ is a source angle;
$\alpha$ is an angle between a horizontal plane and the tilted planes; and
$\Gamma$ is a maximum fan angle of the fan beam.

14. A method in accordance with claim 13 wherein $$g(\gamma - \tilde{\gamma}) = \left(\frac{\gamma - \tilde{\gamma}}{\sin(\eta(\gamma) - \eta(\tilde{\gamma}))}\right)^2 h(\gamma - \tilde{\gamma}) \approx A(\gamma) K(\gamma - \tilde{\gamma}) h(\gamma - \tilde{\gamma}) B(\tilde{\gamma});$$

where h( ) is a parallel kernel and A, B, and K are written as:

$$A(\gamma) = \frac{1 + \cos^2\alpha \tan^2\gamma}{1 + \tan^2\gamma};$$

$$B(\tilde{\gamma}) = \frac{1 + \cos^2\alpha \tan^2\tilde{\gamma}}{1 + \tan^2\tilde{\gamma}};$$

$$K(\gamma - \tilde{\gamma}) = \frac{1 + \tan^2(\gamma - \tilde{\gamma})}{1 + \cos^2\alpha \tan^2(\gamma - \tilde{\gamma})} \times \left(\frac{\gamma - \tilde{\gamma}}{\sin\{a\tan[\cos\alpha \tan(\gamma - \tilde{\gamma})]\}}\right)^2;$$

and $\eta(\gamma) = \arctan[(\cos\alpha) \times \tan(\gamma)]$.

15. A method in accordance with claim 13 wherein said SW($\beta,\gamma$) is an underscan weight function, and said weighting is performed prior to said filtering, and said filtering is performed prior to said backprojection.

16. A method in accordance with claim 13 wherein said SW($\beta,\gamma$) is an overscan weight function, and said filtering is performed prior to said weighting, and said weighting is performed prior to said backprojection.

17. A multi-slice, computed tomography CT imaging system, said imaging system comprising a moveable x-ray source and a curved detector, said system configured to:
move said x-ray source through a trajectory;
project an x-ray cone beam from said moving x-ray source through an object towards said curved detector; and
determine contributions of segments along the trajectory to voxels in a reconstruction volume of the object, including compensating the determined contributions for curvature of said detector and x-ray cone beam geometry.

18. A multi-slice, computed tomography CT imaging system in accordance with claim 17, wherein said system being configured to move said x-ray source through a trajectory comprises said system being configured to move said x-ray source through a helical trajectory relative to the object.

19. A multi-slice, computed tomography CT imaging system in accordance with claim 17 and further wherein said system being configured to determine contributions of segments along the trajectory to voxels in a reconstruction volume of the object comprises said system being configured to filter and backproject using a double integral over a fan angle and source angle for each point in the reconstruction volume.

20. A multi-slice, computed tomography CT imaging system in accordance with claim 19 wherein said system being configured to backproject using a double integral comprises said system being configured to backproject onto a polar reconstruction lattice.

21. A multi-slice, computed tomography CT imaging system in accordance with claim 17, wherein said detector is a cylindrical detector, and said system being configured to compensate the determined contributions for curvature of said detector and x-ray cone beam geometry comprises said system being configured to compensate the determined contributions for curvature of said cylindrical detector.

22. A multi-slice, computed tomography CT imaging system, said imaging system comprising a moveable x-ray source and a curved detector, said system configured to:
move an x-ray source through a trajectory;
project an x-ray cone beam from said moving x-ray source through an object towards a curved detector; and
weight, filter, and backproject a signal representative of detected x-rays passing through the object to produce a tomographic image;
said system further configured to backproject in a three-dimensional space, with compensation for x-ray cone-beam geometry; and wherein said system being configured to backproject using a signal representative of detected x-rays comprises said system being configured to backproject onto a polar reconstruction lattice.

23. A multi-slice, computed tomography CT imaging system in accordance with claim 22, wherein said system is configured to perform said weighting prior to said filtering, and said filtering prior to said backprojecting.

24. A multi-slice, computed tomography CT imaging system in accordance with claim 22 wherein said curved detector is a cylindrical detector.

25. A multi-slice, computed tomography CT imaging system in accordance with claim 22, wherein said system is configured to weight said signal prior to filtering said signal, and to filter said signal prior to said backprojecting.

26. A multi-slice, computed tomography CT imaging system in accordance with claim 25, wherein said system being configured to weight, filter, and backproject a signal representative of detected x-rays passing through the object to produce a tomographic image comprises said system being configured to determine a reconstruction image function $f(v)$ written as:

$$f(v) =$$

$$\int_0^{\pi+2\Gamma} \frac{S}{L^2(v,\beta)} [g \otimes (p^* \times HSW(\beta, \gamma))](\gamma; \xi', \beta) \frac{\cos^{3/2}(\gamma \cos \alpha) d\beta}{(\cos^2\gamma + \sin^2\gamma \cos^2\alpha)^{3/2}}$$

where:

⊗ represents convolution;

S is a source to isocenter distance;

v is a voxel with cylindrical coordinates (r, ψ, κ);

ξ'=ξ' (v,β) is a z-elevation for a projection of v onto a detector;

L is a voxel to source distance (in three-dimensional space);

g( ) denotes a fan-beam reconstruction convolution kernel;

p* is data that has been interpolated onto a tilted plane;

HSW( ) denotes the half-scan weights;

γ is a fan angle;

β is a source angle;

α is an angle between a horizontal plane and the tilted planes; and

Γ is a maximum fan angle of the fan beam.

27. A method in accordance with claim 26 wherein $$g(\gamma - \tilde{\gamma}) = \left(\frac{\gamma - \tilde{\gamma}}{\sin(\eta(\gamma) - \eta(\tilde{\gamma}))}\right)^2 h(\gamma - \tilde{\gamma}) \approx A(\gamma)K(\gamma - \tilde{\gamma})h(\gamma - \tilde{\gamma})B(\tilde{\gamma});$$

where h( ) is a parallel kernel and A, B, and K are written as:

$$A(\gamma) = \frac{1 + \cos^2\alpha \tan^2\gamma}{1 + \tan^2\gamma};$$

$$B(\tilde{\gamma}) = \frac{1 + \cos^2\alpha \tan^2\tilde{\gamma}}{1 + \tan^2\tilde{\gamma}};$$

$$K(\gamma - \tilde{\gamma}) = \frac{1 + \tan^2(\gamma - \tilde{\gamma})}{1 + \cos^2\alpha \tan^2(\gamma - \tilde{\gamma})} \times \left(\frac{\gamma - \tilde{\gamma}}{\sin\{a\tan[\cos\alpha \tan(\gamma - \tilde{\gamma})]\}}\right)^2;$$

and $$\eta(\gamma) = \arctan[(\cos \alpha) \times \tan(\gamma)];$$

and where γ is a fan angle for a ray passing through a voxel being reconstructed.

28. A multi-slice, computed tomography CT imaging system in accordance with claim 22 wherein said system being configured to move said x-ray source through a trajectory comprises said system being configured to move said x-ray source in a helical trajectory relative to the object.

29. A multi-slice, computed tomography CT imaging system in accordance with claim 22, wherein said system being configured to weight, filter, and backproject a signal representative of detected x-rays passing through the object to produce a tomographic image comprises said system being configured to determine a reconstruction image function $f(v) = f(r, \phi, \kappa)$ written as:

$$f(r, \phi, \kappa) =$$

$$\int_0^{2\pi+B\Gamma} \int_{-\Gamma}^{\Gamma} \frac{S}{L^2 + \kappa^2} \frac{l \times SW(\beta, \gamma)}{\cos(\alpha)} g(\gamma - \tilde{\gamma}) p^*(\beta, \gamma, \xi') \cos(\gamma \cos(\alpha)) d\gamma d\beta$$

where:

B denotes an overscan angle;

SW(β,γ) denotes a member of a group consisting of overscan and underscan weight functions;

S is a source to isocenter distance;

v is a voxel with cylindrical coordinates (r, φ, κ);

ξ'=ξ' (v,β) is a z-elevation for a projection of v onto a detector;

L is a voxel to source distance (in three-dimensional space);

g( ) denotes a fan-beam reconstruction convolution kernel;

p* is data that has been interpolated onto a tilted plane;

γ is a fan angle;

γ is a fan angle for a ray passing through a voxel being reconstructed;

β is a source angle;

α is an angle between a horizontal plane and the tilted planes; and

Γ is a maximum fan angle of the fan beam.

30. A multi-slice, computed tomography CT imaging system in accordance with claim 29 wherein said SW(β,γ) is an overscan weight function, and said system is configured to perform said filtering prior to said weighting, and said weighting prior to said backprojection.

31. A method in accordance with claim 29 wherein $$g(\gamma - \tilde{\gamma}) = \left(\frac{\gamma - \tilde{\gamma}}{\sin(\eta(\gamma) - \eta(\tilde{\gamma}))}\right)^2 h(\gamma - \tilde{\gamma}) \approx A(\gamma)K(\gamma - \tilde{\gamma})h(\gamma - \tilde{\gamma})B(\tilde{\gamma});$$

where h( ) is a parallel kernel and A, B, and K are written as:

$$A(\gamma) = \frac{1 + \cos^2\alpha \tan^2\gamma}{1 + \tan^2\gamma};$$

$$B(\tilde{\gamma}) = \frac{1 + \cos^2\alpha \tan^2\tilde{\gamma}}{1 + \tan^2\tilde{\gamma}};$$

$$K(\gamma - \tilde{\gamma}) = \frac{1 + \tan^2(\gamma - \tilde{\gamma})}{1 + \cos^2\alpha \tan^2(\gamma - \tilde{\gamma})} \times \left(\frac{\gamma - \tilde{\gamma}}{\sin\{a\tan[\cos\alpha \tan(\gamma - \tilde{\gamma})]\}}\right)^2;$$

and $$\eta(\gamma) = \arctan[(\cos \alpha) \times \tan(\gamma)].$$

32. A multi-slice, computed tomography CT imaging system in accordance with claim 29 wherein said SW (β,γ) is an underscan weight function, and said system is configured to perform said weighting prior to said filtering, and said filtering prior to said backprojection.

* * * * *

UNITED STATES PATENT AND TRADEMARK OFFICE
CERTIFICATE OF CORRECTION

PATENT NO. : 6,459,754 B1
DATED : October 1, 2002
INVENTOR(S) : Besson et al.

It is certified that error appears in the above-identified patent and that said Letters Patent is hereby corrected as shown below:

Column 12,
Line 53, delete "$\gamma$ is a fan" and insert therefor -- $\tilde{\gamma}$ is a fan --.
Line 55, delete "7" and insert therefor -- 6 --.
Line 59, delete "7" and insert therefor -- 6 --.

Column 13,
Line 6, delete "$\int_{0}^{2\pi+\beta T}$" and insert therefor -- $\int_{0}^{2\pi+B}$ --.

Line 25, delete "$\gamma$ is a fan angle for" and insert therefor -- $\tilde{\gamma}$ is a fan angle for --.

Column 15,
Line 48, delete "$\gamma$ is a fan" and insert therefor -- $\tilde{\gamma}$ is a fan --.

Column 16,
Line 3, delete "$\int_{0}^{2\pi+\beta T}$" and insert therefor -- $\int_{0}^{2\pi+B}$ --.

Line 23, delete "$\gamma$ is a fan angle for" and insert therefor -- $\tilde{\gamma}$ is a fan angle for --.

Signed and Sealed this

Nineteenth Day of April, 2005

JON W. DUDAS
*Director of the United States Patent and Trademark Office*